(12) United States Patent
Claypool

(10) Patent No.: US 9,305,341 B2
(45) Date of Patent: Apr. 5, 2016

(54) SYSTEM AND METHOD FOR MEASUREMENT OF THROUGH SILICON STRUCTURES

(76) Inventor: Christopher L. Claypool, Carlsbad, CA (US)

( * ) Notice: Subject to any disclaimer, the term of this patent is extended or adjusted under 35 U.S.C. 154(b) by 427 days.

(21) Appl. No.: 13/356,336

(22) Filed: Jan. 23, 2012

(65) Prior Publication Data

US 2013/0148877 A1   Jun. 13, 2013

Related U.S. Application Data

(60) Provisional application No. 61/435,117, filed on Jan. 21, 2011.

(51) Int. Cl.
| | |
|---|---|
| G06K 9/00 | (2006.01) |
| G06T 7/00 | (2006.01) |
| G01B 11/22 | (2006.01) |
| G01N 21/25 | (2006.01) |
| H01L 21/66 | (2006.01) |

(52) U.S. Cl.
CPC ............. *G06T 7/0004* (2013.01); *G01B 11/22* (2013.01); *G01N 21/25* (2013.01); *H01L 22/12* (2013.01); *G01B 2210/56* (2013.01)

(58) Field of Classification Search
None
See application file for complete search history.

(56) References Cited

U.S. PATENT DOCUMENTS

| 5,240,550 A * | 8/1993 | Boehnke | H01L 21/31144 216/24 |
|---|---|---|---|
| 6,674,572 B1 * | 1/2004 | Scheruebl | G02B 21/0024 356/237.5 |
| 2010/0204820 A1 * | 8/2010 | Finarov | H01L 21/68728 700/213 |
| 2010/0321671 A1 * | 12/2010 | Marx | G01B 11/22 356/51 |

* cited by examiner

*Primary Examiner* — Jayesh A Patel
(74) *Attorney, Agent, or Firm* — John R. Ross; John R. Ross, III

(57) ABSTRACT

A system and method for measurement of high aspect ratio through silicon via structures. A preferred embodiment includes a white light source and optical components adapted to provide a measurement beam which is nearly collimated with a measurement spot size of the same order of magnitude as the diameter (or effective diameter) of the TSV. These embodiments include a white light source with a variable aperture and other optical components chosen to control the angular spectrum of the incident light. In preferred embodiments the optical components include an automated XYZ stage and a system controller that are utilized to direct the illumination light so as to illuminate the top and bottom of TSV under analysis.

8 Claims, 9 Drawing Sheets

SYSTEM AND METHOD FOR MEASUREMENT OF THROUGH SILICON STRUCTURES

The present invention relates to measurement systems and methods and in particular to such systems and methods for depth measurements of high aspect through silicon structures. This application claims the benefit of Provisional Application 61/435,117 filed Jan. 21, 2011, which is incorporated by reference herein.

BACKGROUND OF THE INVENTION

Field of the Invention

To continue improvements in power efficiency and system performance, semiconductor manufacturers are looking beyond traditional two dimensional scaling strategies towards three dimensional integration. Chip stacking using through-silicon-via (TSV) technology is a key enabling step for three dimensional integrated circuit integration. The TSV is formed by etching a deep via through silicon, depositing an isolation layer on the via side wall, and filling the via with a conductor material such as copper or tungsten. The TSV can be formed before completion of the device (via first/via middle) or after device formation (via last). To make connections to the TSV, the silicon wafer is thinned down to expose the TSV.

Because the three dimensional chip stacking is post wafer fabrication, any yield loss due to the three dimensional integration process will have a significant cost impact on the final system. Since TSV dimensions (microns) differ from typical transistor dimensions (nanometers) by an order of magnitude, additional metrology is required to monitor the TSV fabrication. A quantitative metrology technique that provides non-destructive, high throughput measurements of TSV etch depth and depth uniformity is necessary in the wafer production line to monitor production quality and stability, and to ensure final high device yield.

Various optical techniques have been developed to detect changes in etch depth for process control, including confocal scanning optical microscopy, optical scatterometry techniques, infrared (IR) reflectometry, top-down IR interferometry, and white light interferometry. Although these prior art techniques are capable of measuring etch depth, they are very sensitive to the aspect ratio and are typically not able to reliably measure TSV structures with critical dimension feature sizes in the 1-10 μm range and etch depths of 20 μm or deeper (aspect ratios greater than 20:1) because of signal attenuation. As the via diameter decreases, the TSV aspect ratio increases and there are few non-contact measurement techniques that are suitable for in-line inspection.

There has been a growing demand for measuring high aspect ratio via structures, with diameters less than 30 microns and depths ranging from tens to hundreds of microns. The primary method currently used to measure the etch depth of high aspect ratio TSVs is cross-section scanning electron microscopy (SEM). Because cross-section SEM is time consuming and destructive, it cannot be used as in-line metrology for high volume manufacturing. When the TSV diameter is large (>30 μm), the via's critical dimension and depth can be measured with optical imaging techniques. An imaging based system with a high magnification objective lens (50-100×) and a large focus travel can be used to determine etch depth by sequentially focusing on the top surface and bottom surface of the via. The maximum measurable depth increases with the via's diameter, but decreases with the objectives numerical aperture because the angular spectrum increases which prevents the light from reaching the bottom of the TSV.

Due to the transparency of silicon and other semiconductors in the infrared, IR microscopy has been proposed for the backside measurement of TSV structures. However, the resolution of an IR microscope (typically ≥1 μm) is coarser than a comparable optical microscope since a larger wavelength of light is used. Alternatively, reflectometer technology has gained wide acceptance in semiconductor manufacturing processes for monitoring film thickness. In addition to widespread industry acceptance, normal incidence reflectometry has several technological advantages including stability, accuracy (due to shorter wavelengths than NIR), a wide variety of available light sources, the ability to measure a single via structure, and the ability to measure film thickness and material properties. Ultraviolet reflectometry has been developed for trench depth measurement and conventional reflectometer tools have been used to measure via structures, but challenges remain when measuring high aspect ratio TSV structures because of signal attenuation.

What is needed is a better method for measuring high aspect TSV structures.

SUMMARY OF THE INVENTION

The present invention provides a system and method for measurement of high aspect ratio through silicon via structures. A preferred embodiment includes a white light source and optical components adapted to provide a measurement beam which is nearly collimated with a measurement spot size of the same order of magnitude as the diameter (or effective diameter) of the TSV. These embodiments include a white light source with a variable aperture and other optical components chosen to control the angular spectrum of the incident light. In preferred embodiments the optical components include an automated XYZ stage and a system controller that are utilized to direct the illumination light so as to illuminate the top and bottom of TSV under analysis. In these preferred embodiments a beam splitter directs a portion of the light reflected from the top and bottom of the TSV to a CCD camera for imaging purposes and a portion of the reflected light to a spectrometer equipped with a fixed grating and a linear CCD array. In the preferred embodiments a combination of a slit and a pinhole at the entrance of the spectrometer allows the measurement spot size to be adjusted independently in the x and y dimensions. Preferably the controller automates the collection and analysis of the measured data.

DETAILED DESCRIPTION OF PREFERRED EMBODIMENTS

Figure 1:
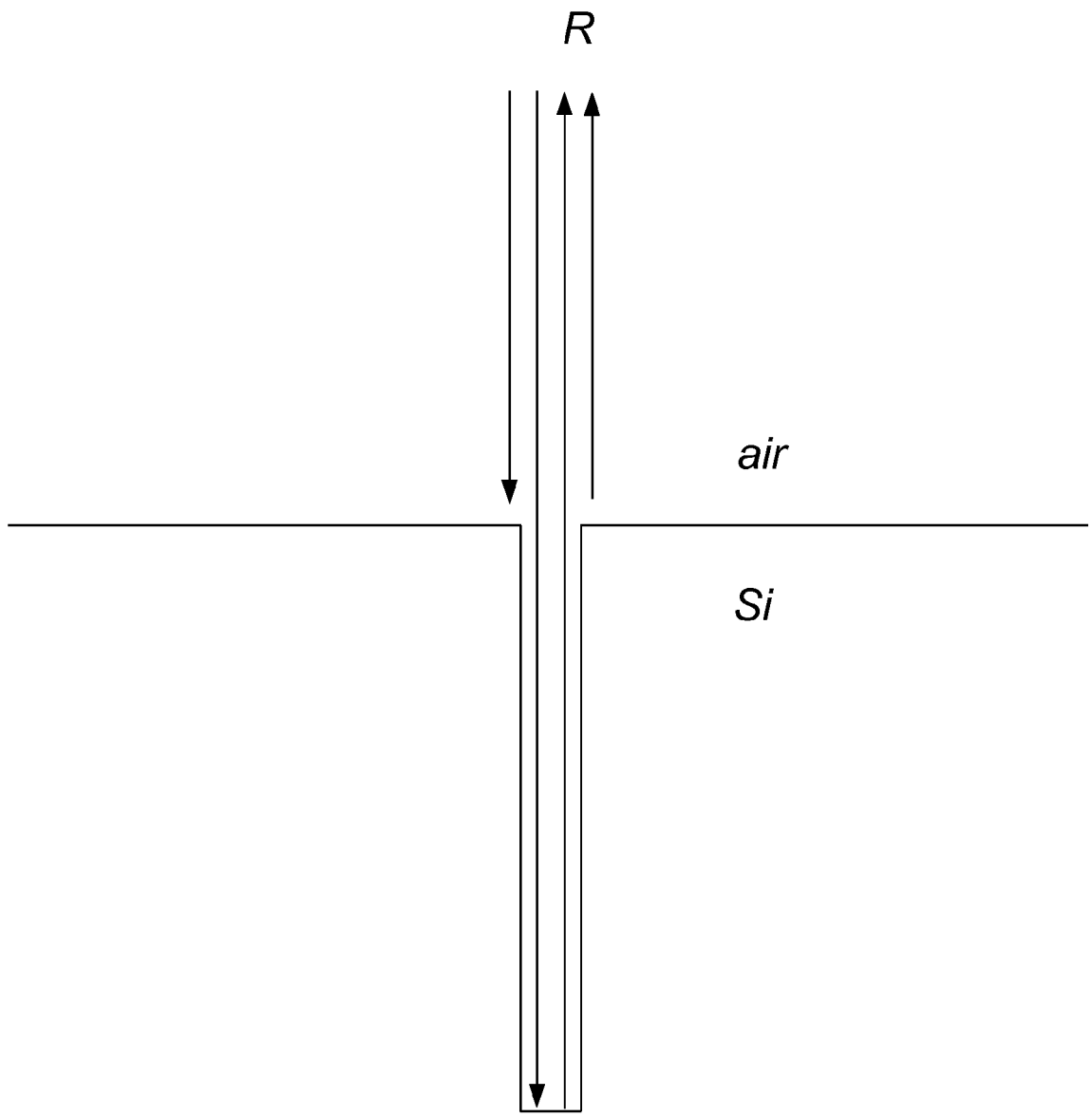
FIG. 1 shows a typical TSV and demonstrates an important feature of the present invention.
Figure 2A:
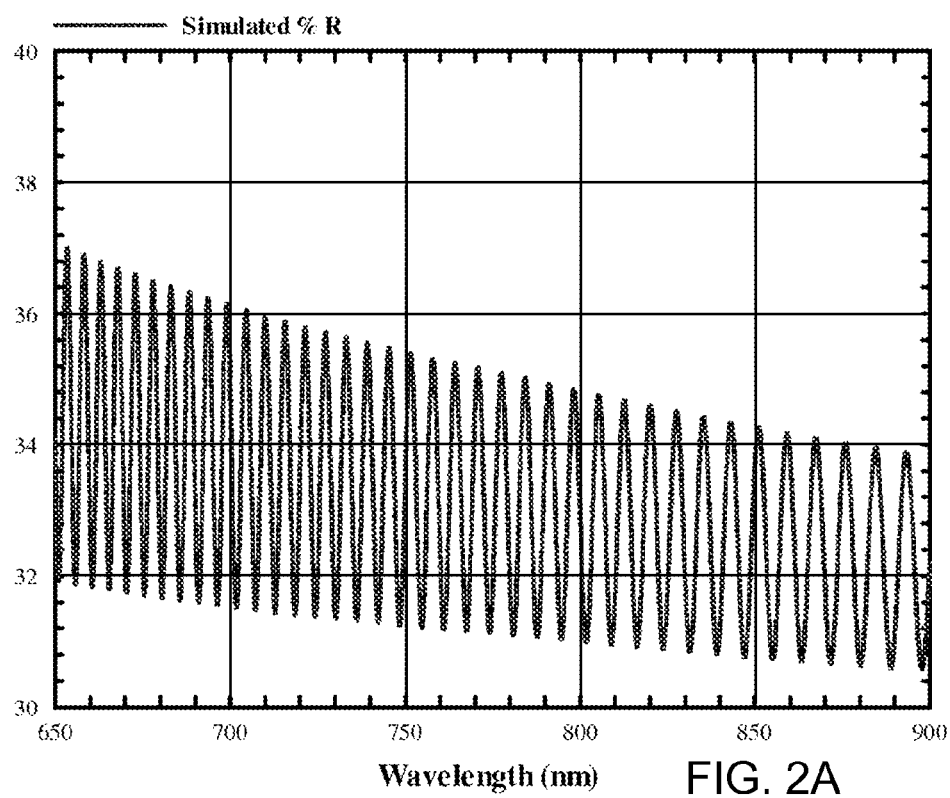
FIGS. 2A and 2B show simulations of reflection spectrum and corresponding power spectral density analysis of features of the present invention.
Figure 2B:
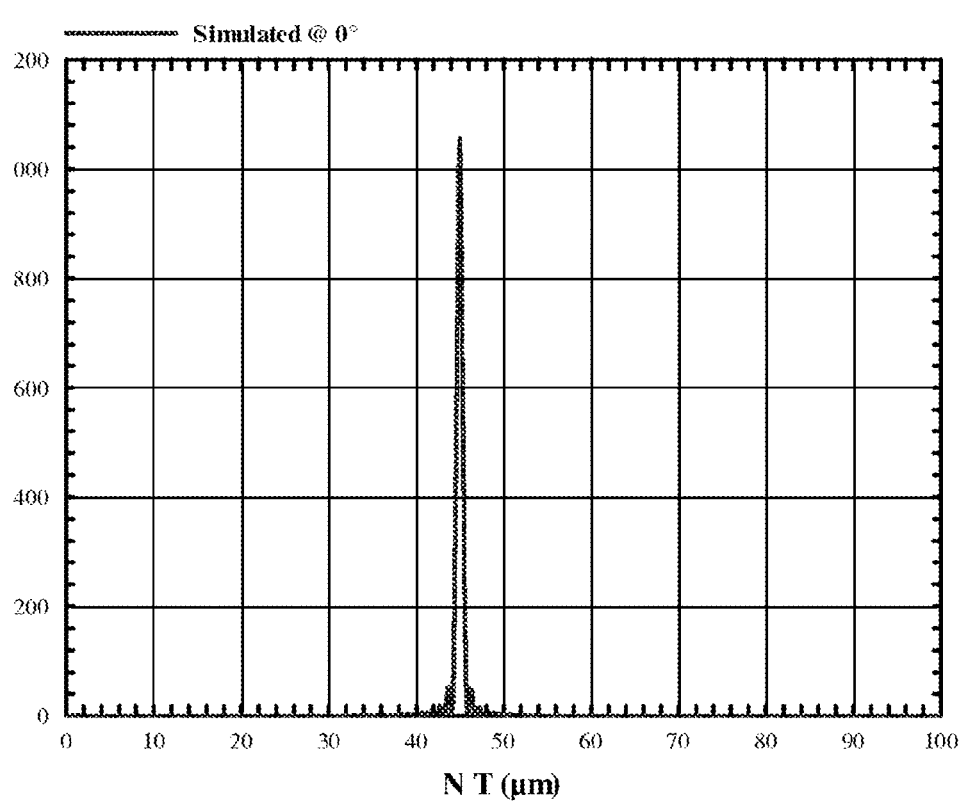

Applicant has developed an optical method based on normal incidence reflectometry to measure the etch depth of high aspect ratio TSV structures. Consider the case of a high aspect ratio TSV structure as shown in FIG. 1. Interference between the light reflected from the top and bottom surface of the via structure occurs due to the optical path difference of the reflected beams. Simulation and analysis of the spectral reflection from TSV structures was performed using SCI's FilmTek™ software, an optical thin film modeling package based on Abelès 2×2 matrix method. A simulated reflection spectrum and Power Spectral Density analysis of the reflection magnitude as a function of frequency for a TSV structure with depth of 45 μm is shown in FIG. 2. The maximum measurable depth and aspect ratio that can be measured for a TSV structure will depend on the wavelength resolution of the linear CCD detector and the coherence of the reflected signal. To achieve the maximum coherence in the reflected signal from the TSV structure, the angular spectrum of the incident and collected light must be small and the fraction of light reflecting from the top and bottom surfaces of the via must be balanced. In other words, the measurement beam must be nearly collimated and the measurement spot size must be of the same order of magnitude as the TSV diameter so that the reflected intensity from the top and bottom surface of the via is balanced and the intensity of the interference in the spectral reflectance is maximized.

Figure 3:
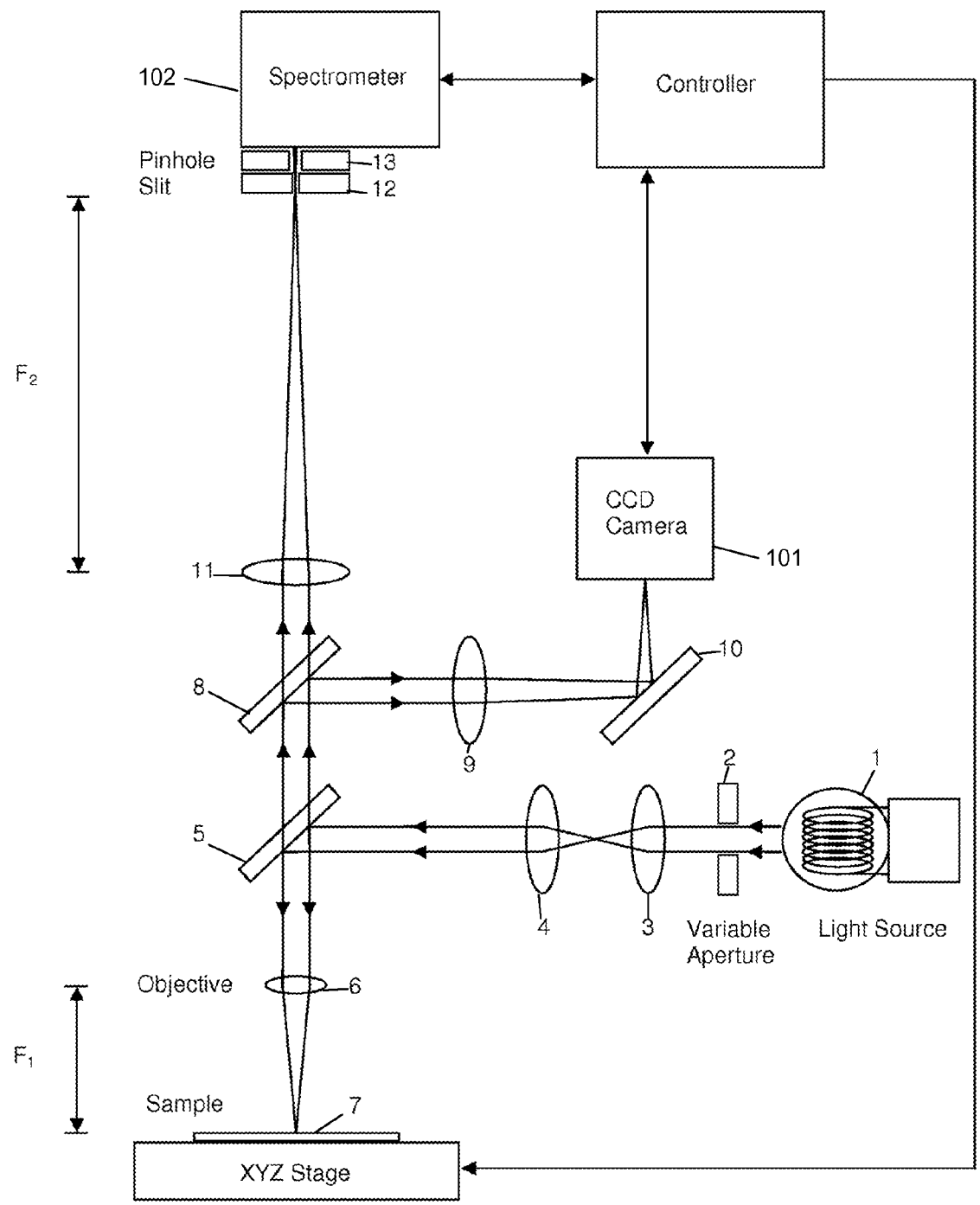
FIG. 3 is a schematic drawing of a preferred measurement in accordance with the present invention.

A preferred measurement apparatus is shown in FIG. 3. A light source 1 is connected to a power supply and emits white light for illumination. The illumination light passes through a variable aperture 2 to control the angular spectrum of the incident light. After the variable aperture, the light is directed through lenses 3, 4 to a beamsplitter 5, and passes through an objective lens 6 to the sample 7 supported by an automated XYZ stage. A low power objective, such as 5× or 10×, in combination with the variable aperture in front of the light source allows the illumination light to reach the top and bottom surface of the via or trench structure. The focal length of the objective lens 6 is defined as $F_1$. After reflecting from the sample of interest, the light is collected by the objective 6 and directed to a beam splitter 8. A fraction of the light is directed through a lens 9 and mirror 10 to a CCD camera 101 for imaging purposes. The remaining light is directed through a lens 11 to a spectrometer 102. The focal length of the spectrometer lens 11 is defined as $F_2$. The magnification of the spectrometer lens 11 and CCD camera lens 9 are not equivalent. In this way, the measurement spot size can be very small while the CCD camera field of view is large for imaging purposes. The spectrometer design preferably utilizes a fixed grating in combination with a linear CCD array. Alternative spectrometer configurations include using a two dimensional CCD array or photodiode array rather than the linear CCD array. Prior to entering the spectrometer, the light passes through a slit 12 and pinhole 13 where the slit is typically of smaller dimension than the diameter of the pinhole. The opening of the slit is aligned perpendicular to the linear CCD array inside of the spectrometer. The combination of the slit and pinhole allows the measurement spot size to be adjusted independently in the x and y dimensions. A central controller automates the collection and analysis of measured data.

The observed coherence of the spectral reflectance from a TSV structure is influenced by a combination of the measurement spot size, angular spectrum of the incident and collected light, and the wavelength resolution of the spectrometer. These design parameters should be optimized in order to accurately measure deep, high aspect ratio TSV structures. In a preferred embodiment, the wavelength resolution of the spectrometer is approximately 0.15 nm, which is sufficient to distinguish oscillations in the reflection spectrum for TSV structures up to 500 μm in depth. The combination of a small variable aperture 2 in front of the light source 1, low power objective 6, and a long focal length ($F_2$) for the spectrometer lens 11 minimizes the angle spread for the incident and collected light.

To measure individual high aspect ratio TSV structures that may be as small as 1 μm in diameter, the light must be nearly collimated and the spot size must be small. The combination of both a slit and pinhole at the entrance to the spectrometer provides independent control of the measurement spot size in x and y dimensions. This design allows the spot size to be optimized for a particular sample type or array of structures. For example, if a single via is to be measured, a nearly symmetrical spot may be ideal. Alternatively, for measuring the depth of a trench, the best signal to noise may be achieved with an asymmetric spot size in which the long axis of the spot is aligned parallel to the direction of the trench. This type of asymmetrical spot size would serve to increase the light collected by the spectrometer while maintaining the excellent coherence of a small, symmetrical spot size.

The measurement spot size can be approximated by the following expression $$\text{Spot Size}(y) = (F_1/F_2)^*(S_y)$$

$$\text{Spot Size}(x) = (F_1/F_2)^*(P_x)$$

where $F_1$ is the focal length of the objective, $F_2$ is the focal length of the spectrometer lens, $S_y$ is the size of the slit opening, and $P_x$ is the size of the pinhole diameter. If no pinhole is used, or if a CCD collection lens is used inside the spectrometer, $P_x$ corresponds to the pixel width of the linear CCD array. Consider a design utilizing a 5× objective with focal length of 40 mm, spectrometer lens with focal length of 400 mm, slit size of 25 μm, and pinhole diameter of 200 μm. From the above expression, the spot size will be approximately 2.5 μm by 10 μm in the in the y and x dimensions, respectively. In this way, an extremely small spot size is achieved without requiring a high magnification objective. Avoiding the use of a high power objective is critical for limiting the angular spectrum of the collected light and maximizing the coherence of the spectral reflection from a high aspect ratio TSV or trench structure.

Figure 4:
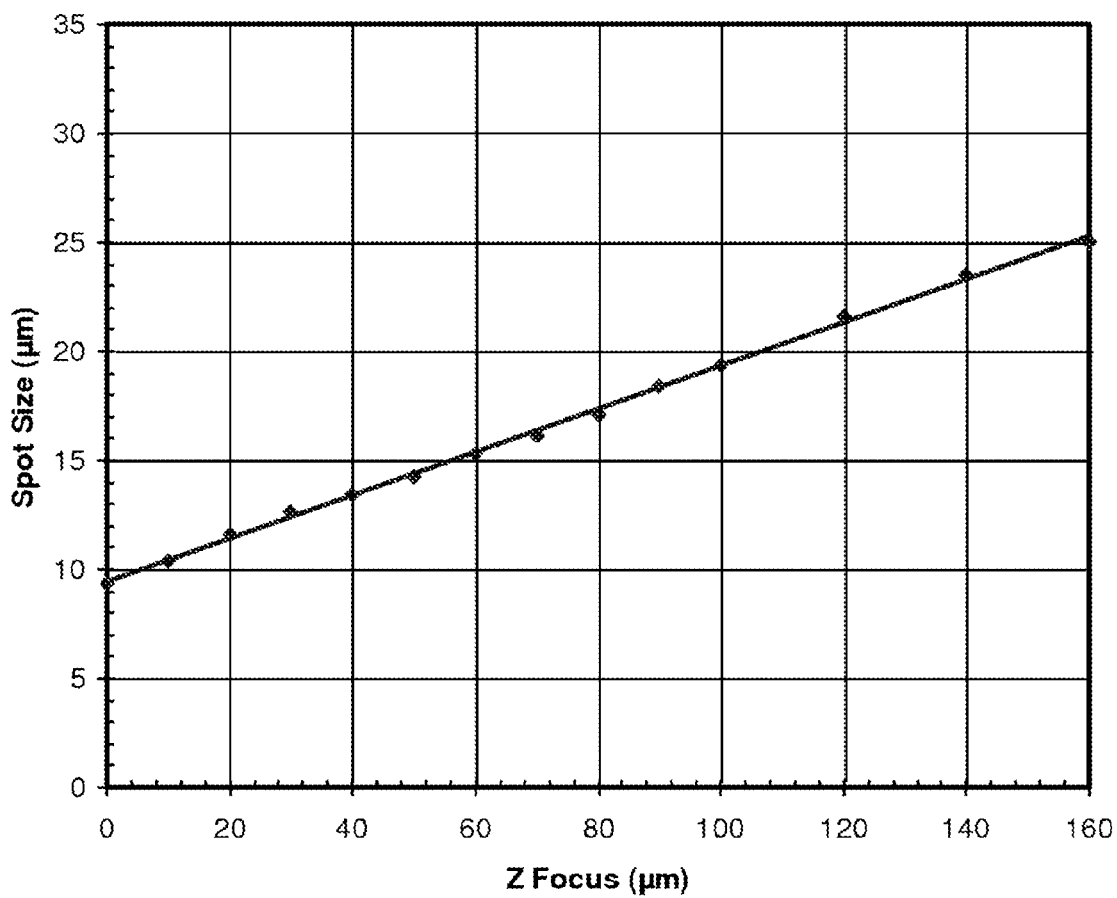
FIG. 4 shows how spot size varies with distance of the target TSV from the location of focus of one of the lenses of a preferred embodiment of the present invention.

The measurement spot size relationship outlined above is valid when the distance between the sample 7 and objective 6 is equivalent to the objective focal length ($F_1$). A linear relationship is observed between the increase in measurement spot size and the distance away from focal length $F_1$ as indicated in FIG. 4. Applicant's approach takes advantage of this effect to optimize the measurement performance for a given TSV diameter or trench width. The intensity of the reflected light from the top and bottom surface of the TSV structure must be balanced in order to maximize the intensity of the interference observed in the spectral reflectance. The maximum coherence of the spectral reflection will generally be achieved when the measurement spot size is of the same order as the TSV diameter or trench width. Consider the previous example where the instrument is configured for a measurement spot size of 2.5 μm by 10 μm. While this spot size may be ideal for measuring high aspect ratio TSV structures with small diameter (e.g., 2 μm), a larger spot size may provide the best signal to noise when measuring larger diameter TSV structures (e.g., 25 μm). Based on the known relationship between focus distance and spot size, the spot size can be adjusted to maximize the observed coherence for a given TSV diameter by automatically moving the stage height prior to measurement. The easily adjustable spot size allows a variety of TSV diameters to be measured while maintaining optimum measurement performance for each structure.

For example, a sample containing a variety of via structures with diameters ranging from 5 to 100 microns would be difficult to measure with a single, fixed measurement spot size. Using conventional pattern recognition techniques, the diameter of the TSV structure of interest can be determined prior to measurement. Based on the measured TSV diameter, the instrument control software moves the stage to the distance away from the focus condition necessary to obtain a measurement spot size of the same order as the TSV diameter. In this way, the optimum measurement performance is automatically achieved for different TSV dimensions.

Figure 5A:
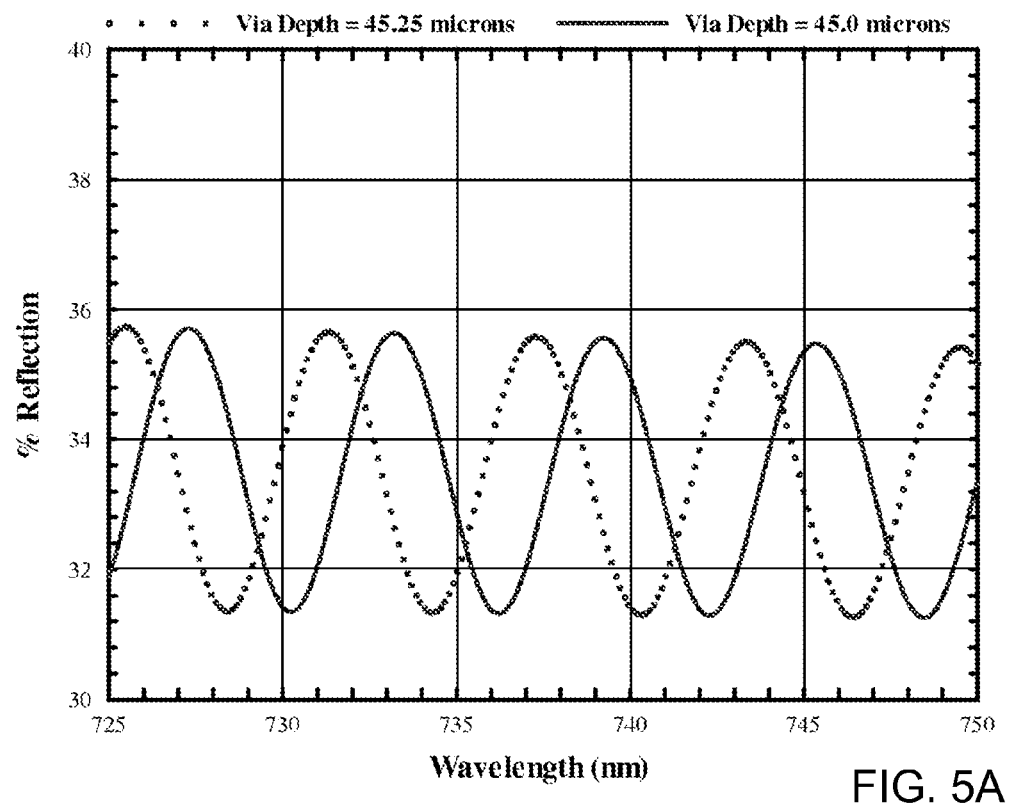
FIGS. 5A and 5B show simulations or percent reflection and power spectral density for two closely differing via depths.
Figure 5B:
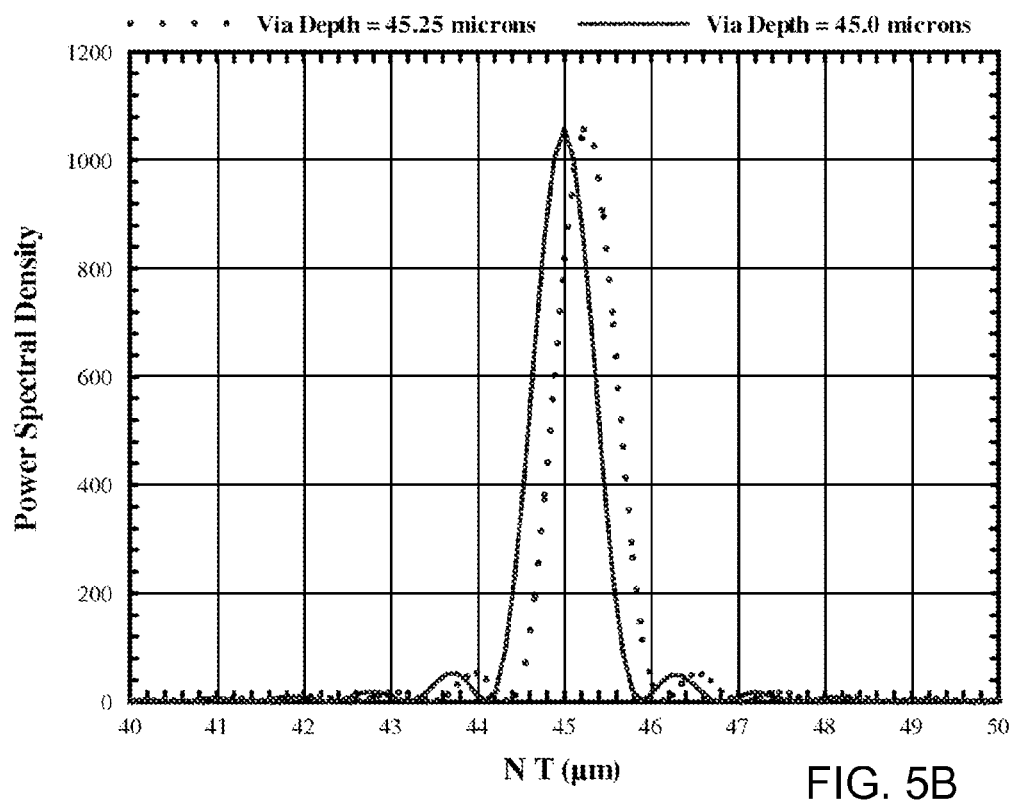

This non-contact and non-destructive measurement apparatus provides accurate and repeatable high-throughput measurements of TSV etch depth and depth uniformity necessary to ensure high yield during TSV fabrication. The sensitivity of the method to small changes in TSV etch depth is illustrated in FIG. 5. Very small changes in TSV etch depth are readily observed by corresponding shifts in the reflection spectra and Power Spectral Density analysis. In the current embodiment of the design, TSV etch depth can be measured for via structures with diameters ranging from 1 to 400 μm, up to a maximum etch depth of 500 μm.

Figure 6:
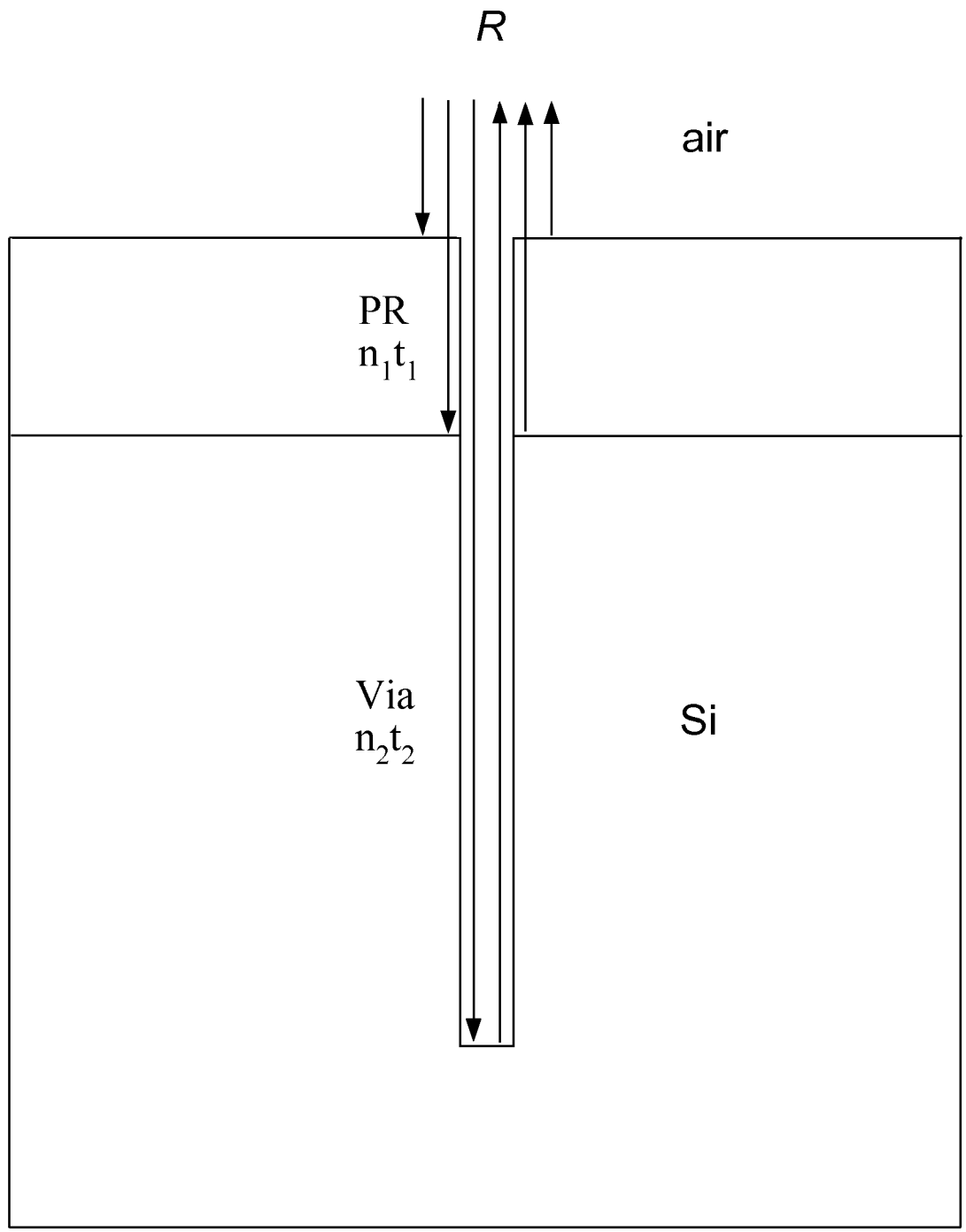
FIG. 6 shows how the present invention can be used to simultaneously determine photoresist thickness and via depth.
Figure 7:
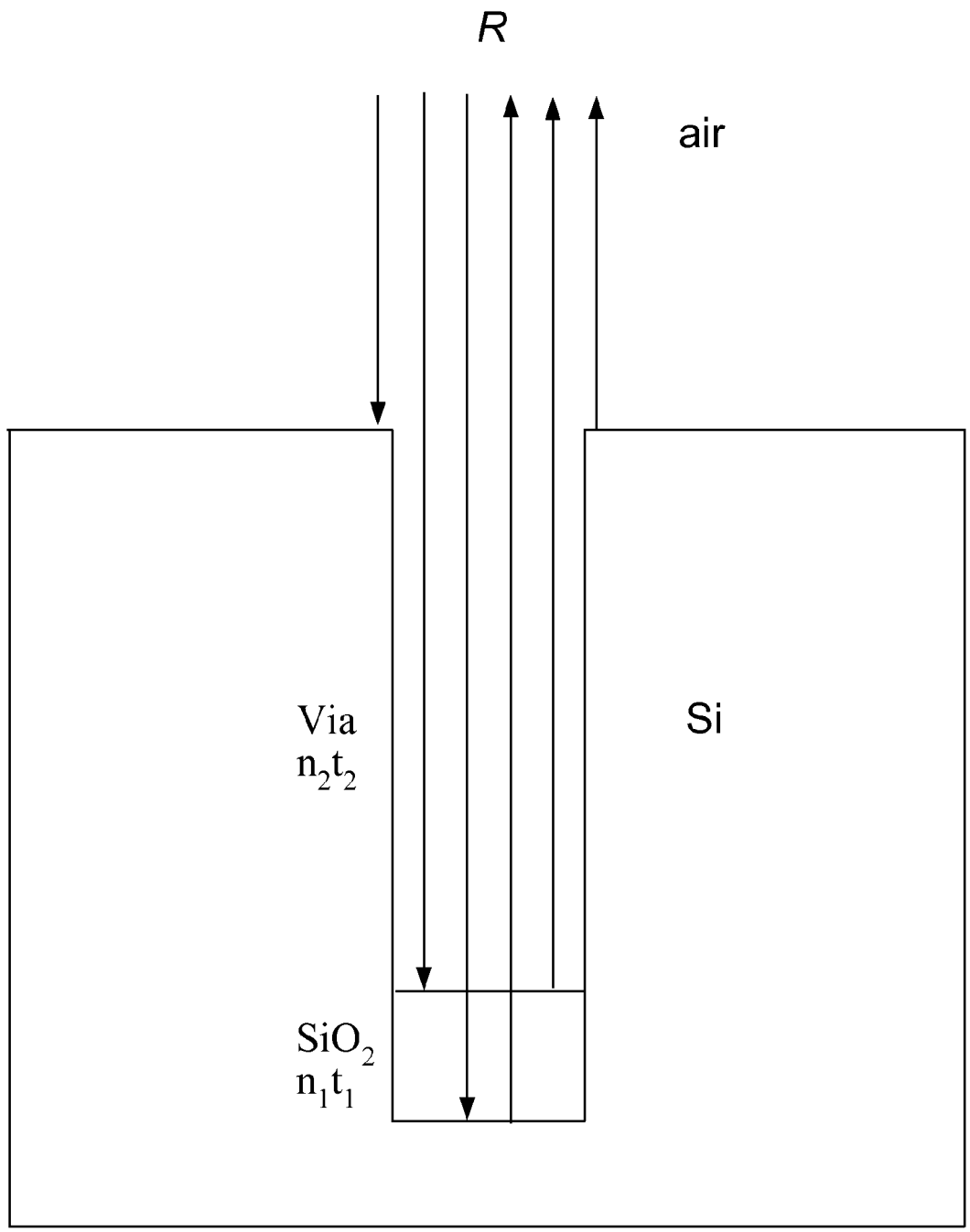
FIG. 7 shows how the present invention can be utilized to simultaneously measure via depth and residual oxide layer at the bottom of the via.

Other measurement applications include the determination of film thickness and etch depth for TSV structures with additional layers. Single or multi-layer film thicknesses in or above the TSV structure can be determined simultaneously with etch depth. Films such as photoresist, nitride, or oxide layers may exist on top of the TSV structure as indicated in FIG. 6. Similarly, the thickness of films located at the bottom of the TSV structure can be measured with the apparatus as shown in FIG. 7. Currently there is considerable interest in the measurement of residual oxide thickness at the bottom of via structures.

Figure 8:
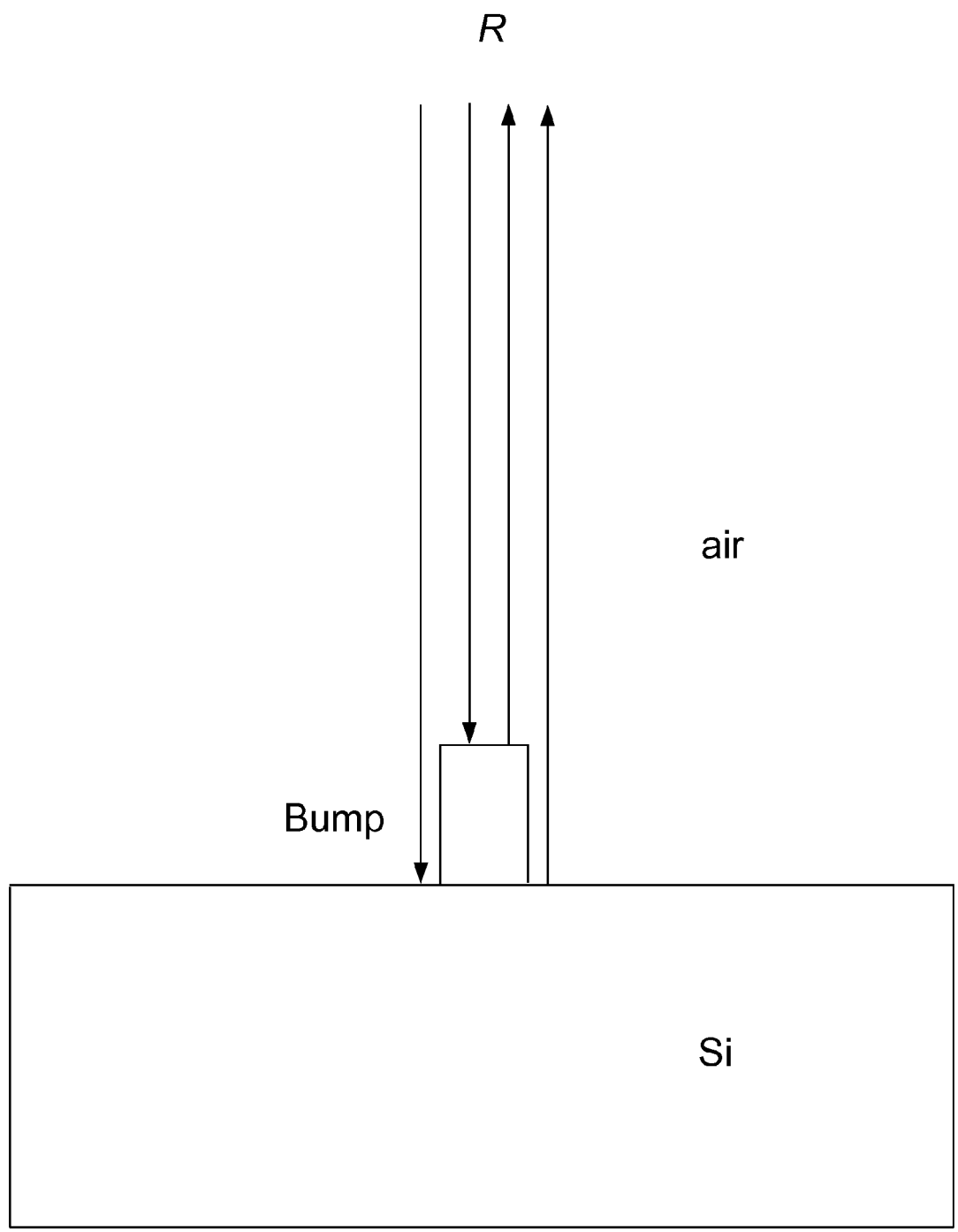
FIG. 8 shows how the present invention can be used to determine bump height.
Figure 9:
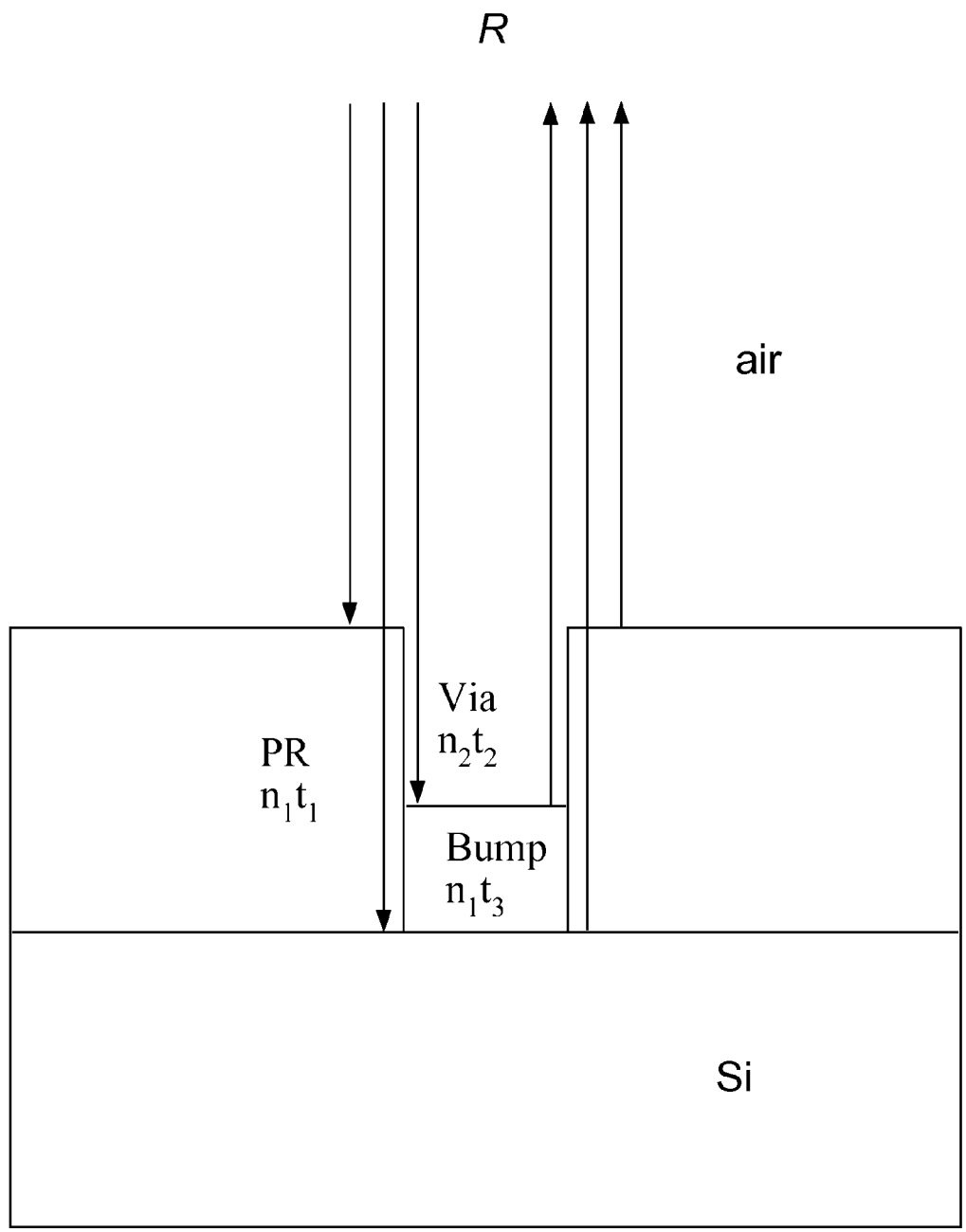
FIG. 9 shows how the present invention can be utilized to measure photoresist thickness, bump height and via depth.

Measurement applications are not limited to TSV structures. For example, the present invention can be used to measure the height and height uniformity of metallic bump and microbump structures as shown in FIG. 8. The simultaneous measurement of bump height, via depth, and photoresist thickness has been successfully demonstrated for bump structures imbedded in photoresist such as is shown in FIG. 9 for bump diameters ranging from 5 to 100 microns, bump height ranging from 5 to 75 microns, and photoresist depth of 75 microns.

Automation for Inline Production

Although the system and method described above can be utilized to measure through silicon structures manually with an operator one at a time, in preferred embodiment the system is a part of an integrated circuit production line and the system is controlled by the controller which includes computer processor features for automatically measuring the features of the through silicon structures and recording the results.

VARIATIONS

While the present invention has been described in terms of specific embodiments, readers should recognize that many modifications and alternatives are possible within the general scope of the present invention. Therefore the scope of the present invention should be determined by the appended claims and their legal equivalence.

What is claimed is:

1. An optical measurement system for measuring high aspect ratio through silicon structures, each high aspect ratio through silicon structure defining a top surface and a bottom surface, with the structures having a variety of sizes etched on an etched side of silicon wafers, said system comprising:
   A) a light source and optical components providing a measurement beam which is nearly collimated and which is adjustable to provide a spot size of the same order of magnitude as the size of the high aspect ratio silicon structure,
   B) an XYZ stage and a system controller adapted to direct illumination from the light source toward the etched side of the wafer so as to illuminate with a beam spot the top and bottom of individual high aspect ratio through silicon structures,
   C) a camera for imaging the high aspect ratio through silicon structures,
   D) a spectrometer for determining depths of individual high aspect ratio silicon structures based on interference between light reflected from the top surface and the bottom surface of the through individual high aspect ratio through silicon structures,
   E) a beam splitter adapted to direct a portion of the light reflected from the wafer to the camera for imaging purposes and light reflected from the top and bottom surfaces of the high aspect ratio through silicon structure to the spectrometer, and
   F) a computer processor for determining depth of the individual high aspect ratio through silicon structures from optical information produced by said camera and said spectrometer, and
   G) a grating and a linear CCD array:
   wherein the spot size is approximated by the following expression:

$$\text{Spot Size}(y) = (F_1/F_2) * (Sy)$$

$$\text{Spot Size}(x) = (F_1/F_2) * (Px)$$

where $F_1$ is the focal length of the objective, $F_2$ is the focal length of the spectrometer lens, Sy is the size of the slit opening, and Px is the size of the pinhole diameter.

2. The system as in claim 1 wherein the high aspect ratio through silicon structure include through silicon via structures.

3. The system as in claim 1 wherein the through silicon structure include through silicon trench structures.

4. The system as in claim 1 wherein the spectrometer also includes a slit and a pinhole.

5. The system as in claim 1 wherein the beam spot defines a size which is on the order of the high aspect ratio through silicon structure.

6. The system as in claim 1 wherein the optical measurement system comprises a 5× objective lens with focal length of 40 mm, and the spectrometer comprises a lens with focal length of 400 mm, a 25 pm slit size, and pinhole diameter of 200 pm to provide a spot size of approximately 2.5 pm by 10 pm respectively in the in the y and x dimensions.

7. The system as in claim 1 wherein the computer processor is also programmed to determine the width of the high aspect silicon structure and its aspect ratio.

8. The system as in claim 1 wherein the system is a part of an integrated circuit production line and the system controller includes computer processor features for automatically measuring the features of the high aspect ratio through silicon structures and recording the results.

\* \* \* \* \*